United States Patent [19]

Verheijen

[11] Patent Number: 6,033,664
[45] Date of Patent: *Mar. 7, 2000

[54] USE OF A PREPARATION COMPRISING A PLASMINOGEN ACTIVATOR TO IMPROVE WOUND HEALING

[75] Inventor: Johan Hendrikus Verheijen, Berkel en Rodenrijs, Netherlands

[73] Assignee: Nederlandse Organisatie voor toegepast-natuurwetenschappelijk onderzoek TNO, Netherlands

[*] Notice: This patent is subject to a terminal disclaimer.

[21] Appl. No.: 09/189,524

[22] Filed: Nov. 10, 1998

Related U.S. Application Data

[63] Continuation of application No. 08/905,874, Aug. 4, 1997, Pat. No. 5,925,350, which is a continuation of application No. 08/590,987, Jan. 24, 1996, abandoned.

[30] Foreign Application Priority Data

Jan. 27, 1995 [EP] European Pat. Off. .............. 95200208

[51] Int. Cl.[7] ........................... A61K 38/48; A61K 38/54
[52] U.S. Cl. ................. 424/94.63; 424/94.3; 424/94.64; 435/212; 435/219; 514/925; 514/928
[58] Field of Search ................................ 424/94.3, 94.63, 424/94.64; 435/212, 219; 514/925, 928

[56] References Cited

U.S. PATENT DOCUMENTS

| | | | |
|---|---|---|---|
| 4,929,442 | 5/1990 | Powell | 424/85.2 |
| 5,192,743 | 3/1993 | Hsu et al. | 514/8 |
| 5,364,622 | 11/1994 | Franz et al. | 424/94.64 |

FOREIGN PATENT DOCUMENTS 0227400  7/1987  European Pat. Off. .

OTHER PUBLICATIONS

M.C. Stacey, et al; "Tissue and Urokinase Plasminogen Activator in the Environs of Venous and Ischaemic Leg Ulcers", The British Journal of Surgery, vol. 80, No. 5, May 1993, pp. 596–599.

Quax et al.; Plasminogen activators are involved in keratinocyte and fibroblast migration in wounded cultures in vitro, Fibrinolysis, vol. 8, pp. 221–228, 1994.

Grondahl–Hansen et al.; J. Invest. Dermatol. vol. 8, pp. 790–795, Abstract 1988.

*Primary Examiner*—Leon B. Lankford, Jr.
*Assistant Examiner*—Christopher R. Tate
*Attorney, Agent, or Firm*—Londa and Traub LLP

[57] ABSTRACT

The present invention relates to the use of non-bacterial plasminogen activators in the manufacture of a topical medical preparation for the treatment of slow- or non-healing wounds. In addition, the present invention relates to a composition comprising a physiologically acceptable carrier and an effective amount of a non-bacterial plasminogen activator, with the exclusion of t-PA. Finally, the present invention is directed to a method of treatment of slow- or non-healing wounds comprising the topical application of a non-bacterial plasminogen activator to the site of a wound.

5 Claims, No Drawings

USE OF A PREPARATION COMPRISING A PLASMINOGEN ACTIVATOR TO IMPROVE WOUND HEALING

This application is a continuation of U.S. Ser. No. 08/905,874 filed Aug. 4, 1997, now U.S. Pat. No. 5,925,350, issued Jul. 20, 1999; which is a continuation of U.S. Ser. No. 08/590,987, filed Jan. 24, 1996, now abandoned.

The present invention relates to preparations comprising plasminogen activators and their use in the treatment of slow- or non-healing wounds. More specifically, the invention relates to the improvement of wound healing, especially in the treatment of persistent, or therapy resistent leg ulcers, bedsores, open burns and other slow- or non-healing wounds.

Slow-healing or non-healing wounds are well-known to the skilled artisan. These wounds frequently occur as a result of many types of trauma, infection by micro-organisms, cancer and many other insults to the skin and tissue. The problems associated with these wounds are not new, but well-known to the person skilled in the art. Historical descriptions go back to over more than two-thousand years (see, e.g., A. Scholz in: Leg Ulcers Diagnosis and Treatment. W. Westerhof, ed. Elsevier, Amsterdam 1993, pp. 5–18).

Although during this long period of time considerable progress in the treatment of these types of wounds was achieved, the basic problem of slow- or non-healing wounds is still existent today. Many therapies have been proposed and developed such as:

1. surgical and enzymatic debridement to remove necrotic tissue;
2. pharmacological treatment usually aimed at improving the blood supply;
3. the now widely used occlusive dressings, which help to maintain the proper moist conditions for healing;
4. various forms of grafting; and
5. more recently developed, often experimental, therapies based on growth factors.

Despite these therapies and combinations thereof, slow wound healing remains a significant medical, economic and social problem. For reviews in this respect, reference is made to "Leg Ulcers Diagnosis and Treatment", W. Westerhof ed. 1993, Elsevier Amsterdam; and "Proteolytic Enzymes and Wound Healing", W. Westerhof, W. Van Scheidt, eds. 1994, Springer Verlag, Berlin).

Of the above-mentioned existing therapies some need special attention in relation to the present invention.

In enzymatic debridement, enzymes are used to clean the wound and remove necrotic tissue. Normally, these enzymes are of a rather aspecific proteolytic nature, since a large variety of components in the necrotic tissue should be removed. Examples of clinically used enzyme preparations comprise:

streptokinase and streptodornase, which enzymes remove proteins and DNA, respectively (see, e.g., Forsling E., Comparison of saline and streptokinase-streptodornase in the treatment of leg ulcers, in Eur. J. Clin. Pharmacol. 1988; 33: 637–638; Stüwe U., Enzymatische Wundreinigung, in Fortschr. Med. 1983; 101: 1883–1888);

fibrinolysin (impure plasmin of animal origin) and deoxyribonuclease (commonly of bovine origin) (see, e.g., Fischer H. et al., Enzymatic debridement in venous ulcers cruris, in Fortschr. Med. 1984; 102: 281–283; Westerhof W. et al., Controlled double-blind trial of fibrinolysin-desoxyribonuclease (Elase) solution in patients with chronic leg ulcers who are treated before antologous skin grafting, in J. Am. Acad. Dermatol. 1987; 17: 32–39);

bovine trypsin (Hellgren L., Cleansing properties of stabilized trypsin and streptokinase-streptodornase in necrotic leg ulcers, in Eur J. Clin. Pharmacol. 1983; 24: 623–628);

bromelain prepared from pineapple juice;

several types of bacterial collagenases or other bacterial proteases; and protease mixtures isolated from krill.

The removal of necrotic debris from slow- or non-healing wounds should reduce the potential of infection, promote wound healing and influence graft take. Research on this area has been going on for a long time already but no major breakthrough has occurred.

Pharmacological treatments have been proposed with the aim of improving the blood supply to the tissue around the wound. In relation to this approach, antiplatelet drugs, such as ticlopidine; anticoagulants, such as heparin; vasodilators; and, more recently, intravascular administration of thrombolytic agents, e.g., streptokinase, urokinase plasminogen activator (u-PA), and tissue-type plasminogen activator (t-PA) have been applied. For an overview of this type of treatment, reference is made to: Chester J., Darmandy J. A. In: Leg ulcers diagnosis and treatment. Westerhof W., ed. Amsterdam: Elsevier 1993, pp. 313–324.

In accordance with the present invention, it has been found that topically administered compounds of the type of non-bacterial plasminogen activators improve the process of wound healing in respect of slow- or non-healing wounds. Preferably, compounds of the type of plasminogen activators of mammalian origin are used in accordance with the present invention.

More in particular, the present invention relates to the use of a plasminogen activator including t-PA in the manufacture of a topical medical preparation for the treatment of slow- or non-healing wounds. Further, the present invention provides a composition for topical application comprising a physiologically acceptable carrier and an effective amount of a plasminogen activator, with the exclusion of t-PA.

It is additionally noted that EP-A-0 227 400 describes that topically administered tissue plasminogen activator inhibits post-surgical adhesion formation. Adhesion formation is a major post-surgical complication. Preferably, t-PA is applied to the site of surgical trauma before wound-healing has begun. It is stated in this prior art document that the use of t-PA is not associated with the wound healing, itself. In fact, adhesion formation is a process occurring inside the body, predominantly in cavities, and is not related to the wound healing as such.

Furthermore, in EP-A-0 261 599, a diverse group of compositions for topical application is described. These compositions comprise a biologically active material and a physiologically acceptable carrier suitable for topical application. Topical preparations comprising t-PA are described for the treatment of heart attack victims.

In accordance with the present invention, it has surprisingly been found that topically administered plasminogen activators improve wound healing. The actual mechanism of this improved wound healing is not known. However, the mechanism is not associated with any fibrinolytic activity or necrotic tissue removal, since the use of the fibrinolytic agent streptokinase does not provide the wound healing effect obtained by the compositions and use according to the present invention.

Plasminogen activators which may be used in accordance with the present invention are of non-bacterial origin and include (pro-)urokinase, tissue-type plasminogen activator, variants or mutants of either of these proteins constructed by, e.g., recombinant DNA technology, glycosylation variants, hybrid-proteins constructed from or containing parts of either or both urokinase or tissue-type plasminogen activator. Since the mechanism of the wound healing in accordance with the present invention is not coupled to any fibrinolytic activity, the term "plasminogen activator" as used in the present text can also comprise plasminogen activator derived constructs, variants or mutants which no longer possess fibrinolytic activity. Further, the plasminogen activators derived from vampire-bats, which are, e.g., described in Gardell et al., Isolation characterization and cDNA cloning of a vampire bat salivary plasminogen activator, J. Biol. Chem. 264 (1989) 17947–17952; Kratzschmar et al., The plasminogen activator family from the salivary gland of the vampire bat desmodus —rotundus—cloning and expression, Gene 105 (1991) 229–237; and in EP-A-0 352 119, can suitably be used in the present invention.

Tissue-type plasminogen activator can be isolated from human tissue, cultured human cells or more desirably produced using recombinant DNA technology in eukaryotic or prokaryotic expression systems which are known to those skilled in the art. Suitable t-PA-type plasminogen activators are, e.g., described in EP-A-0 400 545, EP-A-0 289 508, EP-A-0 227 400, EP-A-0 440 709 and EP-A-0 231 624.

Suitable u-PA's and pro-uPA's have, e.g., been described in Hussain et al., Arch Biochem. Biophys. 220 (1983) 31–38; Stump et al., Purification and characterization of single chain urokinase type plasminogen activator from human cell cultures, J. Biol. Chem. 261 (1986) 1274–1278; Winkler et al. Purification and characterization of recombinant urokinase from *Escherichia coli,* Bio/Technology, 3 (1985) 992–1000; Wun et al., Isolation and characterization of urokinase from human plasma, J. Biol. Chem. 257 (1982);, WP-81/01417 and EP-A-0 139 447.

Preferably t-PA, urokinase, and/or pro-urokinase, and most preferably t-PA or mutants thereof, are brought into a physiologically acceptable carrier to be used in accordance with the present invention.

A preferred embodiment of the present invention is the use of the above-defined plasminogen activators in the treatment of leg ulcers.

In the present description, the terms "topical" and "topical application" refer to the non-systemical administration of the active ingredient to the external surface of the wound for local effect.

The plasminogen activator is topically applied to the wounded area in a suitable form such as a salve, ointment cream, emulsion, foam, suspension or liposome preparation. Aqueous solutions of the plasminogen activator are normally not suitable to be applied topically. Preparations having a higher viscosity, which are smearable, should preferably be used. Many examples of suitable compositions for topical application of an active substance are known in the art.

The compositions used in accordance with the present invention comprise an effective quantity of the active plasminogen activator. Normally, compositions comprising 0.01–5 mg plasminogen activator per gram topical composition are used.

Preferably such a pharmaceutical composition is sterile or aseptic and can be packaged in tubes, bottles or other containers suitable for easy topical application.

The pharmaceutical preparations containing plasminogen activators suitable for topical application can be usefully and advantageously employed in the treatment of humans by topical application of such preparations to wounded areas.

As is usual in this field of the art, the wounded area normally is cleaned before the application of the pharmaceutical composition and properly isolated from the environment by proper wound dressings and bandages. The treatment of slow- or non-healing wounds is more efficient when this cleaning procedure followed by the application of the topical composition is repeated after intervals varying between 1 and 7 days during a time period from 1 day to 4 months, depending on the healing process. The interval, duration of application and dose of the pharmaceutical composition containing a plasminogen activator could be different depending on the agent used, the type of patient and the type of wound. The pharmaceutical composition might be applied as single medication or combined with other useful medications.

It has been found that topical compositions containing a plasminogen activator used to treat patients with leg ulcers resistant to the generally applied treatment as known in the art surprisingly led to wound healing in at least 50% of the cases. It was observed that the fibrin depositions thought to be responsible for the problems with wound healing did not dissolve, although a remarkable improvement of wound healing was observed. This unexpected effectiveness of the treatment not related to dissolution of the extravascular fibrin deposits is not understood.

The present application will be described in further detail, while referring to the following examples.

EXAMPLE 1

Commercially available recombinant tissue-type plasminogen activator (Actilyse™) was dissolved in sterile water at a final concentration of 5 mg/ml.

EXAMPLE 2

An ointment containing tissue-type plasminogen activator, and having the following composition, was prepared:

| | |
|---|---|
| 4.8 ml | cetomacrogol wax |
| 4.0 ml | paraffine subliq. |
| 7.2 ml | vaseline white |
| 2.0 ml | propylene glycol |
| 1.2 ml | 0.9% w/v sodium chloride solution in water |
| 0.8 ml | Actilyse™ solution prepared as in example 1 |

The cetomacrogol wax, paraffine and vaseline were molten and stirred during cooling. To the cold mixture propyleneglycol, sodiumchloride solution and Actilyse™ solution were added subsequently with continuous mixing.

EXAMPLE 3

An ointment containing tissue-type plasminogen activator and having the following composition was prepared:

| | |
|---|---|
| 4.8 ml | cetomacrogol wax |
| 2.0 ml | paraffine subliq. |
| 2.2 ml | vaseline white |
| 1.0 ml | propylene glycol |
| 9.2 ml | 0.9% w/v sodium chloride solution in water |
| 0.8 ml | Actilyse™ solution prepared as in example 1 |

EXAMPLE 4

An ointment containing tissue-type plasminogen activator, and having the following composition, was prepared:

| | |
|---|---|
| 4.8 ml | cetomacrogol wax |
| 4.0 ml | paraffine subliq.4.2 ml vaseline white |
| 2.0 ml | propyleneglycol |
| 4.2 ml | 0.9% w/v sodiumchloride solution |
| 0.8 ml | Actilyse™ solution as described in example 1 |

EXAMPLE 5

In order to test the release rate of tissue-type plasminogen activator (t-PA) from the preparations for topical application as described in examples 2, 3 and 4, small defined quantities of ointment (2–30 mg) were applied to 1 cm² pieces of filter paper. Subsequently, the pieces of filter paper were incubated in 1 ml of a buffer containing 0.1 mol/l Tris-HCl pH 7.5, 0.1% w/v Tween-80™ during 24 h at room temperature. The concentration of active t-PA in the buffer was determined with a suitable activity assay and the amount of t-PA in the liquid phase was expressed as a percentage of the amount originally present in the defined quantity of ointment.

Alternatively, the amount of t-PA antigen as determined with a specific immunoassay was determined in the solution and compared with the original amount in the ointment.

For the ointment with the composition of example 2, it was found that 0.9±0.3% of t-PA activity and 1.0±0.4% of t-PA antigen was released in 24 h. For the ointments of examples 3 and 4, a release of 8.9±2.4% and 6.7±3.4% was found in a 24 h period. The good agreement between activity and antigen release indicates that the activity of the t-PA is retained in the ointment.

EXAMPLE 6

The stability of t-PA in the various ointment preparations of examples 2–4 during storage at 4° C. was determined by measuring the enzyme activity, according to the filter paper procedure as described in example 5, before and after a year of storage. It was found that over 60% of the t-PA activity was still present in the preparation after one year of storage.

EXAMPLE 7

Six patients with therapy resistent leg ulcers were treated with an ointment described in example 3 according to the following protocol. A single batch of ointment was prepared and divided in small tubes which were stored at 4° C. until use. The total treatment period was 12 weeks. During the treatment, new pressure gradient bandages were applied twice a week. At these occasions, 0.1 ml to 0.3 ml of t-PA ointment, depending on the size of the ulcer, were evenly applied to the wound surface. The wound was covered with a hydrocolloid dressing and a standard pressure gradient bandage. Criteria for inclusion of patients in the test were chronic clean venous ulceration of the leg confirmed by photo-plethysmography. No patients with a history of diabetes mellitus, congestive heart failure or malignancy were included. Patients with arterial disease and a ankle/branch index of less than 0.75 were excluded, as well. The sizes of the ulcers to be treated varied between 1.8 to 5.1 cm².

All patients suffered from chronic ulcers which had persisted during regular therapy for 6 to 24 months (average 16 months) before admission to the study.

At 0, 4, 8 and 12 weeks, evaluations took place. At the start and after 12 weeks of treatment or after healing, when within 12 weeks, besides evaluation small biopsies were taken and immunohistochemically analysed for fibrin cuffs, using a fibrin specific monoclonal antibody (monoclonal antibody Y22, described in Wasser et al, An antifibrin monoclonal antibody useful in immunoscintigraphic detection of thrombi., Blood 74 (1989) 708–714) and established procedures.

All patients completed the study. No adverse events were noted.

With three of the six patients, the ulcers had completely healed within the 12 week period (one within four weeks, two within eight weeks). The other three patients did not respond to therapy within this time period. Most remarkably in both groups with completely and not completely healed wounds no or only a very slight reduction in fibrin cuffs could be observed.

I claim:

1. A method of treatment of slow- or non-healing wounds comprising the topical application of a composition comprising at least one non-bacterial plasminogen activator selected from the group consisting of urokinase, a urokinase mutant, prourokinase, a prourokinase mutant, and plasminogen activator derived from vampire-bats, as the active ingredient therein, in a sufficient amount to the surface of the slow- or non-healing external wound to treat the slow- or non-healing wound.

2. The method of treatment of claim 1, wherein the plasminogen activator is urokinase.

3. The method of treatment of claim 1, wherein the plasminogen activator is present in a physiologically acceptable carrier.

4. The method of treatment of claim 1, wherein the wounds are leg ulcers.

5. A method of treatment of slow- or non-healing wounds consisting of the topical application of a composition consisting essentially of at least one non-bacterial plasminogen activator selected from the group consisting of urokinase, a urokinase mutant, prourokinase, a prourokinase mutant, and plasminogen activator derived from vampire-bats, present in a pharmaceutically acceptable carrier, in a sufficient amount to the surface of the slow- or non-healing external wound to treat the slow- or non-healing external wound.

* * * * *